United States Patent [19]

Nack et al.

[11] Patent Number: 5,226,197
[45] Date of Patent: Jul. 13, 1993

[54] TONGUE HYGIENE DEVICE

[76] Inventors: Rachel Nack; Robert L. Nack, both of 17 Cullen Dr., West Orange, N.J. 07052

[21] Appl. No.: 944,249

[22] Filed: Sep. 14, 1992

[51] Int. Cl.⁵ .............................. A46B 5/02
[52] U.S. Cl. ............................. 15/111; 15/160; 132/309; 606/161
[58] Field of Search .............. 15/110, 111, 117, 160, 15/167.1; 128/62 A; 606/161; 132/309

[56] References Cited

U.S. PATENT DOCUMENTS

| | | | |
|---|---|---|---|
| D. 99,352 | 4/1936 | Grapp | 15/110 |
| 301,644 | 7/1884 | Thompson | 15/117 |
| 697,336 | 4/1902 | Hagerty | 606/161 |
| 888,138 | 5/1908 | Bell | 15/110 |
| 1,125,532 | 1/1915 | Himmel | 15/110 |
| 1,128,139 | 2/1915 | Hoffman | 15/111 |
| 1,191,556 | 7/1916 | Blake | 15/117 |
| 1,598,224 | 8/1926 | Van Sant | 15/167.1 |
| 1,728,956 | 9/1929 | Darmitiel | 128/304 |
| 1,891,864 | 12/1932 | Barrett | 15/111 |
| 2,042,239 | 5/1936 | Planding | 15/110 |
| 2,049,956 | 8/1936 | Greenberg . | |
| 2,218,072 | 10/1940 | Runnels | 606/161 |
| 2,253,210 | 8/1941 | Psiharis | 15/110 |
| 2,405,029 | 7/1946 | Gallanty et al. . | |
| 2,574,654 | 11/1951 | Moore . | |
| 2,651,068 | 9/1953 | Seko | 15/111 |
| 3,254,356 | 6/1966 | Yao et al. | 15/111 |
| 3,943,592 | 3/1976 | Bhaskar et al. | 15/160 |
| 4,079,478 | 3/1978 | Andrews | 15/210.1 |
| 4,364,142 | 12/1982 | Pangle | 15/111 |
| 4,455,704 | 6/1984 | Williams | 15/111 |
| 4,488,327 | 12/1984 | Snider | 15/111 |
| 4,610,043 | 9/1986 | Vezjak | 15/111 |
| 4,638,521 | 1/1987 | Potente et al. | 15/117 |
| 5,005,246 | 4/1991 | Yen-Hui | 15/111 |
| 5,061,272 | 10/1991 | Reese | 606/161 |

FOREIGN PATENT DOCUMENTS

| | | | |
|---|---|---|---|
| 734846 | 10/1932 | France | 606/161 |
| 2639 | of 1888 | United Kingdom | 15/111 |
| 17643 | of 1911 | United Kingdom | 15/111 |
| 438071 | 11/1935 | United Kingdom | 15/110 |
| 495982 | 11/1938 | United Kingdom | 15/111 |
| 554286 | 6/1943 | United Kingdom | 15/117 |

Primary Examiner—Harvey C. Hornsby
Assistant Examiner—Mark Spisich

[57] ABSTRACT

A tongue cleaning brush/scraper comprising an elongated handle, one end of which is rounded and wider then the head of a conventional toothbrush, extending from said head a plurality of short bristles. Attached to the end of said rounded head, and extending at the same angle and to the same height as the short bristles is a semi-rigid scraper. When used, the invention will efficiently and quickly clean the tongue while not eliciting the gag reflex.

2 Claims, 2 Drawing Sheets

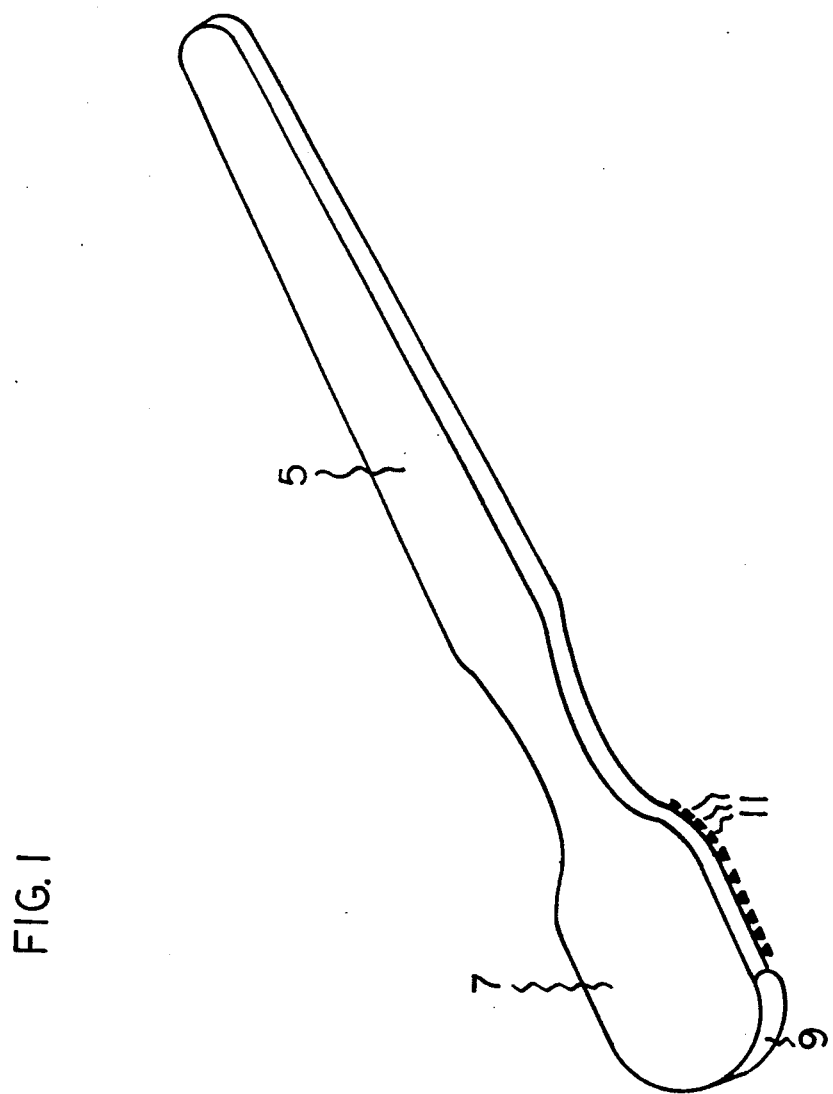

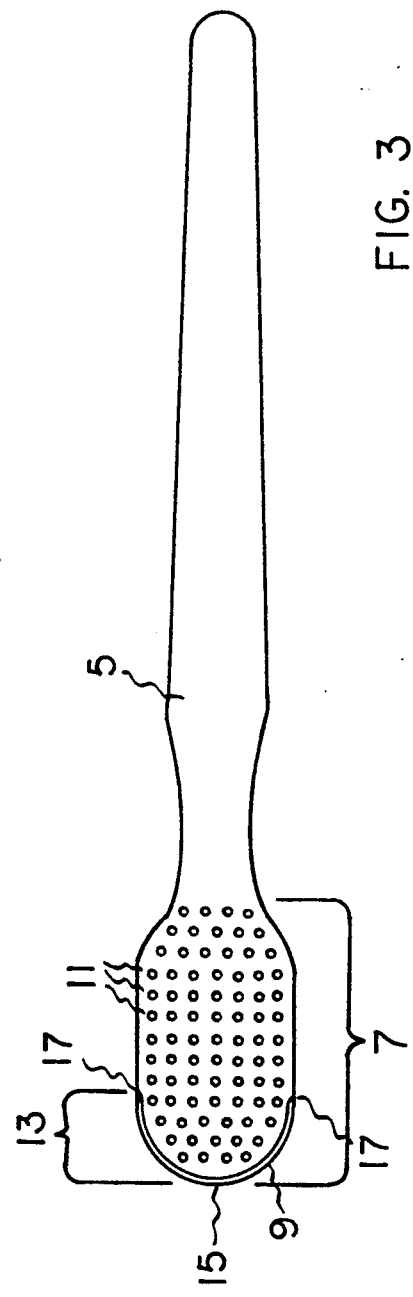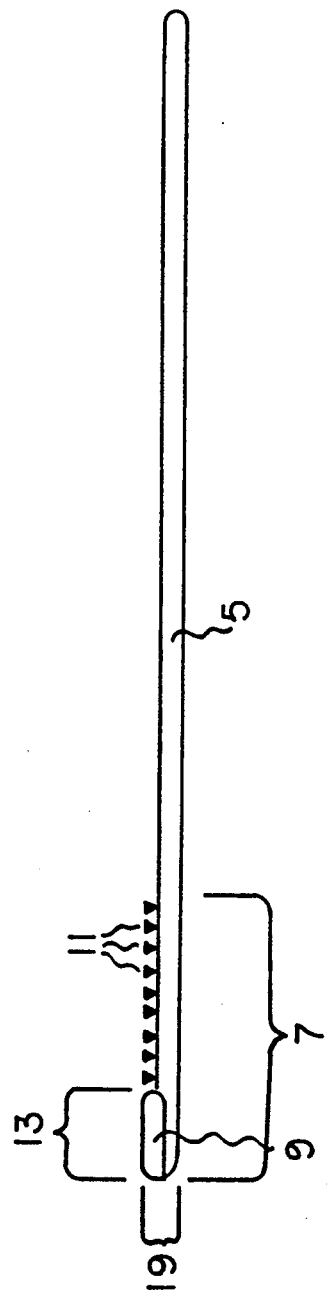

TONGUE HYGIENE DEVICE

BACKGROUND

1. Field of Invention

This invention relates to a device, comprising a handle, a brush, and a scraper, designed to quickly and efficiently clean the tongue, while not eliciting the gag reflex.

2. Description of Prior Art

Heretofore, tongue cleaners consisted of conventional toothbrushes, a variety of tongue scrapers, tongue brushes with different fibrous cleaning members, and even the inverted bowl of a spoon. (Ralph, Aust. Dent. J., 1988; 33(3):224) None of these previous devices, except conventional toothbrushes and spoons, are available at this time, for purchase, by the general public. As an active dentist in a large group private practice, I can attest, first-hand, to the need for a tongue cleaner as a part of one's general oral hygiene regimen. We believe our tongue cleaning invention is the answer to this sorely lacking necessity.

The tongue is an extremely mobile mass of striated muscle covered by mucous membrane. The tongue can change it's shape rapidly and extensively in performing it's functions due to this striated muscle.

The mucous membrane covering the anterior 2/3's (body) and apex (tip) of the tongue is rough, because it is thickly covered with papillae. The posterior ⅓ (pharyngeal) has an uneven or nodular surface due to a number of rounded elevations or nodules. On both sides or margins are a number of vertical folds, but few, if any papillae. Taste buds are found mostly on the tongue, and to a lesser extent, on the soft palate, pharynx, and epiglottis. At the posterior aspect of the body of the tongue are from 8 to 12 circumvallate papillae arranged in a V-shaped row. The greatest number of taste buds are located in the furrows or grooves which surround these papillae. A few taste buds can also be found on the fungiform and foliate papillae, located anteriorly to the circumvallate papillae. The majority of papillae on the body of the tongue are the filiform papillae, which provide friction for the handling of food. The presence of papillae, folds, and grooves on the dorsal surface of the tongue make it a prime location for the retention of debris.

To properly clean the irregular surface of the tongue, a brush is needed to adequately reach the bottom of all the folds, grooves, etc. and loosen this debris. In addition, the tongue is a site for the accumulation of material from sinus drainage (Hugh Bateman, PHD, A Clinical Approach to Speech Anatomy and Physiology, p 64) and can acquire a viscous coating. (Ralph, Aust. Dent. J., 1988; 33(3); 224) A semi-rigid scraper is the ideal tool for removing this type of debris and also to scrape away the material that the brush dislodges.

To complicate matters, a tongue cleaning device, to do it's job properly, must not elicit the "gag reflex". This reflex will preclude individuals from cleaning the tongue as far posteriorly as possible. The pharynx, soft palate, or posterior portion of the tongue can elicit gagging. The importance of this is that any tongue cleaning device must be thin enough so as not to trigger gagging by touching the pharynx or soft palate. Consequently, the area of the tongue we are most concerned with, the anterior ⅔'s, can be properly cleaned only by a device which comprises a brush, scraper, and is thin in design.

As recently as 1986, the Journal of the American Dental Association, in an article on oral hygiene, recommended clean the tongue with a normal toothbrush. (J.A.D.A.; 1986, Special Issue; Guide to Dental Health 6–7)

U.S. Pat. No. 4,079,478 discloses a tongue brush with a fibrous cleaning member which slides along a support frame. It appears to be too complicated and expensive to mass produce. In addition, it has no scraper and because of it's design, which encompasses a sliding, disposable, removeable, fibrous cleaning element, a scraper cannot be incorporated into the device properly. U.S. Pat. Nos. 5,061,272, 4,488,327, 2,405,029, 5,005,246, 4,455,704, 2,651,068, 2,049,956, 2,574,654, 3,254,356, and 1,728,956 all disclose a tongue scraper of some type and design, but no specific thin brush to gain access to and clean the folds, grooves, etc., of the tongue. Some have embodied a conventional toothbrush (e.g. longer bristles) into the device as a combination toothbrush/tongue scraper. Others just have a tongue scraper.

U.S. Pat. No. 1,891,864 discloses a combination tongue brush and scraper, but it's inventor, Cornelius P. Barrett, specifies that the "brushes are concaved which materially facilitates the tongue cleaning operation". It's important to note again that the tongue is an extremely mobile mass of striated muscle, which can change it's shape rapidly and extensively. We feel that approximately even length bristles will much more efficiently and easily clean the tongue with a motion analagous to brushing teeth rather than an arcing motion, superiorly-inferiorly, necessitated by Mr. Barrett's device. Also, the 90 degree edges of both the brush head and scraper, could possibly damage or injure the tissues of the oral cavity when used. In addition, no mention of thinness in design to negate the gag reflex is made. Finally, it's doubtful that the plethora of pins and bolts necessary in the manufacturing of this device, would make it feasible to produce and become available to the general public.

U.S. Pat. No. 3,943,592 embodies a tongue depressor with a Velcro tape attached to one end with a "vertical profile not exceeding 3 millimeters". However, there in no tongue scraper present, we question how well the "over 400 hooks per square inch" will clean around the papillae and in the grooves of the tongue compared to bristles, and we're concerned that the "base fabric" of the Velcro tape would be a medium conducive to the growth of various microorganisms because the fabric would be difficult to clean and dry.

OBJECTS AND ADVANTAGES

Accordingly, it is an object of the present invention to provide a tongue cleaner which can remove food, debris, plaque, etc. from the multitude of grooves, furrows, papillae, etc. on the dorsal surface of the tongue.

It is a further object of the present invention to provide a tongue cleaner which can scrape sinus drainage or other viscous coating off the tongue, in addition to the debris removed from the tongue's grooves, etc. by the brush component.

It is yet a further object of the present invention to provide a tongue cleaner which is thin enough in design so as not to elicit the gag reflex precluding proper cleaning of the tongue.

It is yet a further object of the present invention to provide a tongue cleaner with no sharp corners or edges which can possibly damage tissues in the oral cavity during the cleaning process.

The final object of the present invention is to provide a tongue cleaner which because of it's simplicity in design, will be feasible to manufacture inexpensively and become available to the general public for use as part of their oral hygiene regimen.

The device of the present invention includes an elongated handle, one end of which is rounded and wider than the head of a conventional toothbrush. The said handle, except for the widened end, is of approximately the same dimensions as a conventional toothbrush handle. This will ensure the device can be stored, when not in use, as would a toothbrush. Plastic, such as that used in the manufacturing of conventional toothbrushes, would be an appropriate material from which to make the handle. Extending from the widened surface or head of said handle are short bristles of equal height. These bristles will serve the purpose of cleaning debris, plaque, and bacteria from the grooves, furrows, and papillae on the dorsal surface of the tongue. Conventional wisdom would dictate these bristles, although shorter than those found on standard toothbrushes, be made from the same material. While this may be the case, there are a variety of other materials, such as rubber, plastics, etc., which would also be suitable.

Extending from the distal end or side of said widened head, at the same angle and to the same height as said bristles, is a semi-rigid scraper to scrape and remove any viscous coating on the tongue and the debris loosened by said brush component. Either a type of plastic or rubber (such as those used in a squeegee), would be an appropriate material from which to fabricate the scraper component. While we do not wish to be limited to an exact measurement or dimension, suffice to say that the distance from the distal tip of the scraper and bristles to the back of the widened head of the handle, should be significantly less than the same distance on a conventional toothbrush, which is about 15-17 millimeters. The thinness of the scraper and brush components will ensure the device, when in use, does not touch the pharynx or soft palate, triggering the gag reflex.

All external edges and corners of the invention are softly rounded with no sharp, potentially injurious surfaces present.

The simplicity of the design and the proposed potential materials which could be used in the fabrication of the invention, lend themselves to a manufacturing cost of approximately the same as a standard toothbrush. In addition, because of no springs, bolts, sliding components, crevices, fabrics, etc., the device can be cleaned and stored hygienically, after use, as is a conventional toothbrush.

Readers will find further objects and advantages of the invention from a consideration of the ensuing description and the accompanying drawings.

BRIEF DESCRIPTION OF THE DRAWINGS

In the drawings:

FIG. 1 is a perspective view of the Tongue Hygiene Device.

FIG. 2 is a top plan view of the present invention of FIG. 1.

FIG. 3 is a side elevational view of the present invention of FIG. 1.

DETAILED DESCRIPTION OF THE PREFERRED EMBODIMENT

Referring to FIG. 1 in detail, the perspective view of the Tongue Hygiene Device, the elongated handle 5, has a rounded, widened end, referred to as the head 7 of the handle. Extending from one widened side of said head 7 of the handle, are a plurality of short bristles 11. Integrally affixed to the widened distal end of said head 7 of the handle, is a semi-rigid scraper 9.

Referring to FIG. 2 in detail, the top plan view of the present invention, the important features to notice are a) the extent to which the scraper 9 is affixed and extended around the entire rounded distal end of the head 7 of the handle, and b) the plurality of short bristles 11, extending along the head 7 of the handle, into the concavity formed by the scraper 9.

Referring to FIG. 3 in detail, the side elevational view of the present invention, reference number 13 indicates the horizontal linear distance of scraper 9, measured from the most distal end 15 of the head 7 of the handle, to the scraper's termination points 17, as referred to in FIG. 2. The important feature in note in FIG. 3 is the distance 19 from the distal edges of the bristles 11 and scraper 9, to the back of the widened side of the head 7 of the handle from which the bristles 11 emerge. This is defined as being substantially less than the same measurement on a conventional toothbrush.

It's also important to note on FIGS. 1, 2, and 3, there are no sharp edges or corners on the device which can damage the oral mucosa when the invention is in use.

OPERATIONS OF INVENTION

In operation, the Tongue Hygiene Device is grasped, in either the right or left hand, by the handle 5. The rounded, widened head 7 of the handle, is inserted into the mouth as would a conventional toothbrush. With the scraper 9 and bristles 11 facing interiorly towards the dorsal surface of the tongue, the device is moved in a posterior-anterior direction along said dorsal surface of the tongue. The bristle component 11 of the present invention, will loosen and clean debris, plaque, food, etc., from the grooves, furrows, and papillae of the dorsal surface of the tongue, similar to a toothbrush removing plaque from teeth. With the same said posterior-anterior movement, the scraper component 9 will be removing not only any viscous coating on the dorsal surface of the tongue, but also said debris loosened by said bristle component 11. The cleaning process should encompass the entire dorsal surface of the tongue as far posteriorly as possible. Because of the short design of the device 19, the dorsal surface of the tongue will be cleaned, efficiently and quickly, without triggering the gag reflex. Simple rinsing, as would be done after brushing and flossing one's teeth, will remove the debris from the oral cavity. The present invention can also, as one would with a conventional toothbrush, be rinsed and stored hygienically, in a conventional toothbrush holder, after use.

Thus, the reader will see that the Tongue Hygiene Device provides as efficient, quick, and economical means to clean the dorsal surface of the tongue.

Although the present invention has been described in connection with a preferred embodiment, it is to be understood that one skilled in the art can suggest changes in form, construction, and materials which would, nevertheless, come within the spirit of the invention, and the scope of the following claims.

We claim:

1. A device for cleaning the tongue comprising:

an elongated handle having first and second opposite ends;

a brush head fixed to said first end and having a substantially flat first side;

a plurality of bristles extending from said first side, said plurality of bristles being of substantially equal length each of which has free ends which terminate in a plane spaced from and parallel to said first side;

a semi-rigid scraper mounted on said first side, said scraper having a height substantially equal to that of the bristles and also wherein the scraper terminates above the first side in substantially the same plane defined by the free ends of the bristles, said scraper being located at a free end of said head and having a generally arcuate configuration and which further defines a pocket in which some of said bristles are located;

whereby said bristles and scraper together act to loosen and remove debris located on the tongue.

2. The tongue cleaning device of claim 1 wherein the free end of the head has a substantially rounded configuration so as not to damage to oral cavity during use.

* * * * *